US00PP37444P2

(12) United States Plant Patent
Murillo

(10) Patent No.: US PP37,444 P2
(45) Date of Patent: May 26, 2026

(54) ***SANSEVIERIA* PLANT NAMED 'Crystal Flame'**

(50) Latin Name: *Sansevieria trifasciata*
Varietal Denomination: Crystal Flame

(71) Applicant: Leonardo Murillo, Alajuela (CR)

(72) Inventor: Leonardo Murillo, Alajuela (CR)

( * ) Notice: Subject to any disclaimer, the term of this patent is extended or adjusted under 35 U.S.C. 154(b) by 0 days.

(21) Appl. No.: 19/289,547

(22) Filed: Aug. 4, 2025

(51) Int. Cl.
*A01H 5/12* (2018.01)
*A01H 6/00* (2018.01)

(52) U.S. Cl.
USPC ..... Plt./382

(58) Field of Classification Search
USPC ..... Plt./382
See application file for complete search history.

(56) References Cited

U.S. PATENT DOCUMENTS

PP29,871 P3 * 11/2018 Monge ..... A01H 6/00
Plt./382

OTHER PUBLICATIONS https://www.facebook.com/groups/203949674927368/posts/1008657724456555/ (posted for sale Mar. 19, 2025) (retrieved online Aug. 26, 2025).*

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Sansevieria* plant named 'Crystal Flame', characterized by its upright and conical plant shape; numerous sturdy and long linear leaves with acuminate apices; and leaves that are glossy and dark green in color with contrasting silvery green to light green-colored leaf margins.

2 Drawing Sheets

Figure 1:
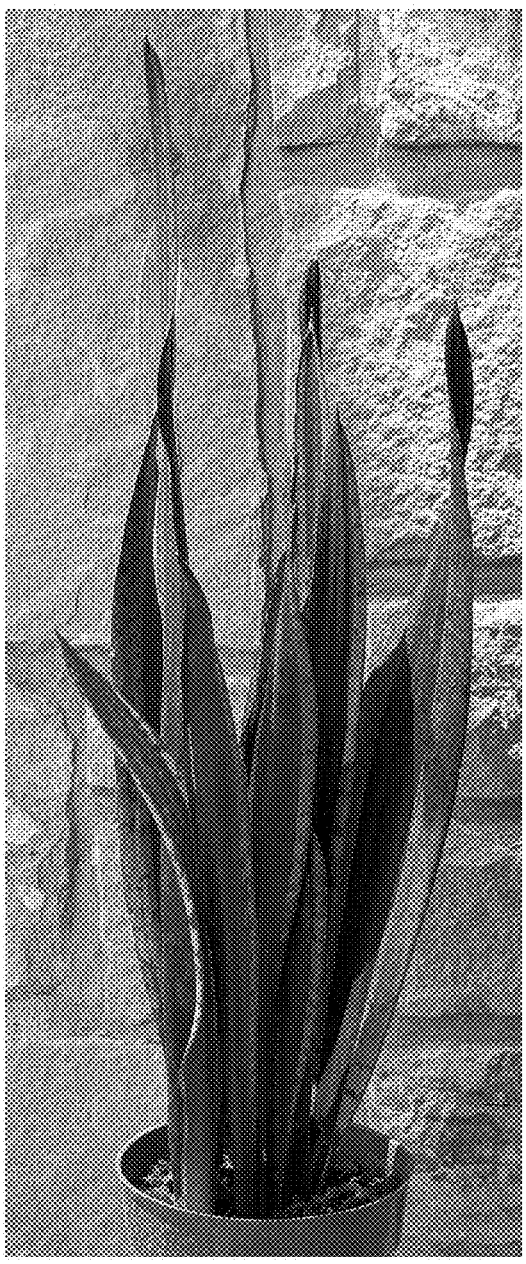

Botanical designation: *Sansevieria trifasciata.*
Cultivar denomination: 'CRYSTAL FLAME'.

BACKGROUND OF THE INVENTION

The present invention relates to a new and distinct cultivar of *Sansevieria* plant, botanically known as *Sansevieria trifasciata* and hereinafter referred to by the name 'Crystal Flame'.

The new *Sansevieria* plant is a naturally-occurring whole plant mutation of *Sansevieria trifasciata* 'Black Gold', not patented. The new *Sansevieria* plant was discovered and selected by the Inventor in March, 2014 as a single plant from within a population of plants of 'Black Gold' in a controlled environment in Alajuela, Costa Rica.

Asexual reproduction of the new *Sansevieria* plant by cuttings and divisions in a controlled environment in Alajuela, Costa Rica since March, 2014 has shown that the unique features of this new *Sansevieria* plant are stable and reproduced true to type in successive generations of asexual reproduction.

SUMMARY OF THE INVENTION

Plants of the new *Sansevieria* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Crystal Flame'. These characteristics in combination distinguish 'Crystal Flame' as a new and distinct *Sansevieria* plant:

1. Upright and conical plant shape.
2. Numerous sturdy and long linear leaves with acuminate apices.
3. Leaves that are glossy and dark green in color with contrasting silvery green to light green-colored leaf margins.

Plants of the new *Sansevieria* differ primarily from plants of the mutation parent, 'Black Gold', in the following characteristics:

1. Plants of the new *Sansevieria* are taller than plants of 'Black Gold'.
2. Plants of the new *Sansevieria* are more upright than and not as outwardly flared as plants of 'Black Gold'.
3. Leaves of plants of the new *Sansevieria* are dark green in color with contrasting silvery green to light green-colored margins whereas leaves of 'Black Gold' are dark green in color with yellow-colored margins.

Plants of the new *Sansevieria* can be compared to plants of *Sansevieria trifasciata* 'Black Coral', not patented. In side-by-side comparisons, plants of the new *Sansevieria* differ primarily from plants of 'Black Coral' in leaf color as leaves of plants of the new *Sansevieria* are dark green in color with contrasting silvery green to light green-colored margins whereas leaves of 'Black Coral' are dark green in color with light greyed green-colored cross-banding and/or chevrons.

BRIEF DESCRIPTION OF THE PHOTOGRAPHS

The accompanying photographs illustrate the overall appearance of the new *Sansevieria* plant showing the colors as true as it is reasonably possible to obtain in colored reproductions of this type. Colors in the photographs may differ slightly from the color values cited in the detailed botanical description which accurately describe the colors of the new *Sansevieria* plant.

The photograph on the first sheet (FIG. 1) is a side perspective view of a typical plant of 'Crystal Flame' grown in a container.

Figure 2:
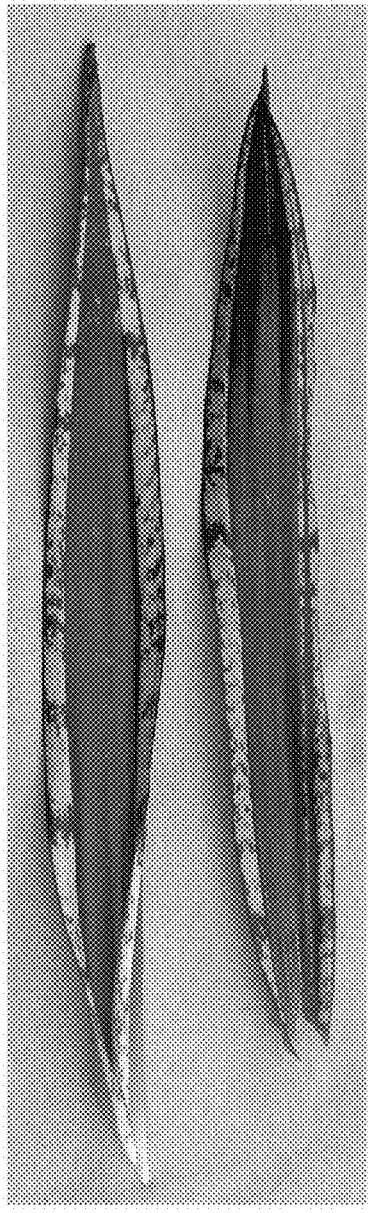

The photograph on the second sheet (FIG. 2) is a close-up view of the upper surface of typical developing leaves of 'Crystal Flame'.

DETAILED BOTANICAL DESCRIPTION

The aforementioned photographs and following observations and measurements describe plants grown in 15-cm containers during the spring in a polypropylene shade cloth-covered greenhouse in Miami, Florida. Plants were grown under environmental conditions and cultural practices which approximate those generally used in commercial *Sansevieria* production. During the production of the plants, day temperatures averaged 32° C., night temperatures averaged 26° C. and light levels averaged 3,000 foot-candles. Plants were six months from planting rooted young plants when the photographs and the detailed description were taken. In the following description, color references are made to The Royal Horticultural Society Colour Chart, 2015 Edition, except where general terms of ordinary dictionary significance are used.

Botanical classification: *Sansevieria trifasciata* 'Crystal Flame'.

Parentage: Naturally-occurring whole plant mutation of *Sansevieria trifasciata* 'Black Gold', not patented.

Propagation:

*Type*.—By leaf cuttings.

*Time to initiate roots, summer*.—About three days at temperatures about 29° C.

*Time to initiate roots, winter*.—About seven days at temperatures about 18° C.

*Time to produce a rooted young plant, summer*.—About three months at temperatures about 29° C.

*Time to produce a rooted young plant roots, winter*.—About four months at temperatures about 18° C.

*Root description*.—Medium in thickness, fibrous; typically orangish white in color, actual color of the roots dependent on substrate composition, water quality, fertilizer, substrate temperature and age of roots.

*Rooting habit*.—Moderately freely branching; medium density.

Plant description:

*Plant and growth habit*.—Upright and conical plant shape; numerous sturdy and long linear leaves with acuminate apices.

*Plant height, from soil level to top of leaf plane*.—About 54 cm.

*Plant diameter or spread*.—About 21 cm.

Leaf description:

*Arrangement*.—Basal; simple.

*Length*.—About 54 cm.

*Width*.—About 5 cm to 7 cm.

*Shape*.—Linear

*Apex*.—Acuminate.

*Margin*.—Entire; not undulate.

*Texture and luster, upper and lower surfaces*.—Smooth, glabrous; coriaceous; glossy.

*Venation pattern*.—Parallel.

*Color*.—Developing leaves, upper and lower surfaces: Centers, close to N189A and towards the base, close to 146A; towards the margins, close to 189B, 189C and N189D with random flecks, close to N189A. Fully expanded leaves, upper and lower surfaces: Centers, close to N189A and towards the margins, close to 146A with random flecks, close to N189A.

Inflorescence description: To date, inflorescence development has not been observed on plants of the new *Sansevieria*.

Pathogen & pest resistance: To date, plants of the new *Sansevieria* have not been observed to be resistant to pathogens or pests common to *Sansevieria*.

It is claimed:

1. A new and distinct *Sansevieria* plant named 'Crystal Flame' as herein illustrated and described.

* * * * *